(12) United States Patent
Filser et al.

(10) Patent No.: US 7,077,391 B2
(45) Date of Patent: Jul. 18, 2006

(54) HOLDING DEVICE FOR A CERAMIC BLANK

(75) Inventors: Frank Filser, Oberengstringen (CH); Ludwig Gauckler, Schaffhausen (CH); Peter Kocher, Wallisellen (CH); Heinz Luethy, Neuchâtel (CH); Peter Schaerer, Zurich (CH); Heiner Hoerhold, Budingen (DE); Peter Kreuder, Bad Nauheim (DE); Stefan Fecher, Johannesberg (DE)

(73) Assignee: Eidgenossische Technische Hochschule Zurich Nichtmetallische Werkstoffe, Zurich (CH)

( * ) Notice: Subject to any disclaimer, the term of this patent is extended or adjusted under 35 U.S.C. 154(b) by 188 days.

(21) Appl. No.: 10/433,722

(22) PCT Filed: Dec. 3, 2001

(86) PCT No.: PCT/CH01/00692

§ 371 (c)(1),
(2), (4) Date: Jun. 3, 2003

(87) PCT Pub. No.: WO02/45614

PCT Pub. Date: Jun. 13, 2002

(65) Prior Publication Data

US 2004/0072121 A1 Apr. 15, 2004

(30) Foreign Application Priority Data

Dec. 7, 2000 (CH) .............................................. 2388/00

(51) Int. Cl.
*B23Q 3/00* (2006.01)

(52) U.S. Cl. ....................................................... 269/287
(58) Field of Classification Search ................. 269/287, 269/289 R; 29/281.1, 235
See application file for complete search history.

(56) References Cited

U.S. PATENT DOCUMENTS

| 4,647,414 | A | * | 3/1987 | Mizuno et al. ............. 264/667 |
| 5,275,987 | A | * | 1/1994 | Newkirk et al. ............ 501/127 |
| 5,342,696 | A | * | 8/1994 | Eidenbenz et al. ....... 428/542.8 |
| 5,939,211 | A | | 8/1999 | Mormann |
| 5,989,106 | A | * | 11/1999 | Tanaka et al. ................ 451/49 |
| 2004/0072121 | A1 | * | 4/2004 | Filser et al. .................. 433/25 |

FOREIGN PATENT DOCUMENTS

| DE | 44 36 231 | 9/1995 |
| EP | 0 807 422 | 11/1997 |
| EP | 0 982 009 | 3/2000 |

* cited by examiner

*Primary Examiner*—Lee D. Wilson
(74) *Attorney, Agent, or Firm*—Bachman & LaPointe, P.C.

(57) ABSTRACT

A holding device comprises a cylindrical or prismatic, porous ceramic blank and elements for clamping in a machine tool for processing the blank by removing material, in order to produce a ceramic workpiece. A narrow frame is fixed by an adhesive connection over at least part of the periphery of the blank, which is held without stresses, in the area of a plane encompassing the longitudinal middle axis (A) of the blank. The frame only covers a small part of the surface of the blank and can be detached and held in a stable holder with a clamping adapter, in such a way that it cannot slide. The entire combination is fixed in the machine tool in such a way as to be resistant to twisting and sliding. The ceramic workpiece emerges continuously form the ceramic blank without predetermination of the advance direction, until holding segments which can then only be freely selected according to number and location have been formed. The holding segments end on the residual material of the blank in the area of the frame or on the frame itself. The holding device is used especially as a workpiece for producing fully ceramic dental prostheses, particularly crowns or bridges.

13 Claims, 3 Drawing Sheets

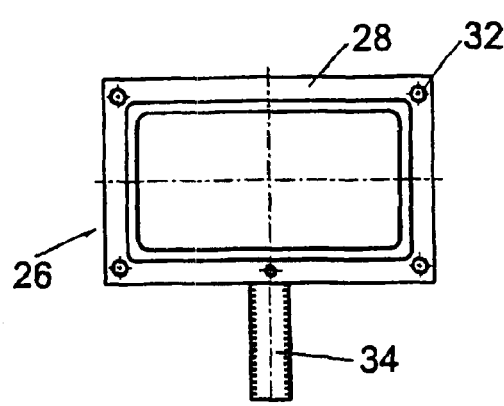
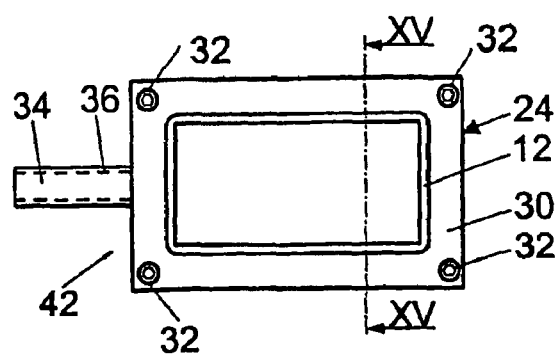
Fig. 13
Fig. 14
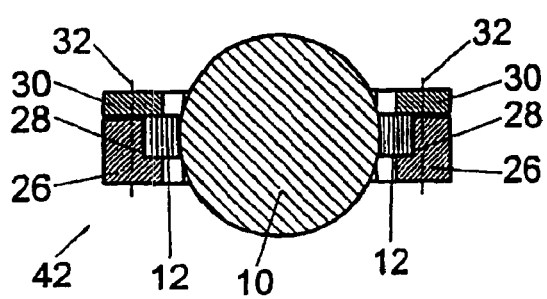
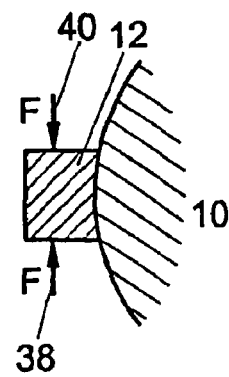
Fig. 15
Fig. 16

HOLDING DEVICE FOR A CERAMIC BLANK

BACKGROUND OF THE INVENTION

The invention relates to a holding device comprises a cylindrically or prismatically formed porous ceramic blank and means for clamping the holding device in a machine tool for the material-removing machining of the blank to produce a ceramic workpiece. The invention also relates to a method for the material-removing machining of a blank in a holding device and a use for a holding device.

In the production of a ceramic workpiece the enlarged form is worked out of the still porous, premanufactured ceramic blank, which is green or sintered on. The enlarged workpiece is then imperviously sintered. In the process it shrinks to the final form, in which the impervious ceramic workpiece agrees with the mass of a model pattern or a drawing. According to another variation, the ceramic workpieces are worked out of the porous ceramic blank in the original size and the porosity is then closed by infiltration.

Porous ceramic blanks are easy to machine in a material-removing manner as they have not yet attained their final hardness. Therefore, they are also very sensitive in the porous state to all mechanical stresses, such as for example pulling, pressure, bending, torsion, impact and shock stress. However, during machining blanks have to tolerate precisely such stresses. Therefore, these porous ceramic blanks need holding devices especially equipped for their machining which during machining take particular account of the sensitivity of the blanks. The mechanical stresses during machining have to be minimised and reliably diverted into the holding device.

These holding devices are in turn clamped on the rotary shaft of a suitable machine tool for the material-removing machining of the blank for production of the ceramic workpiece. The ceramic workpiece is worked out of the blank with special machining tools. This takes place with at least one respective milling, drilling or grinding tool, for example with a respective milling cutter for the coarse and fine machining. Machining generally takes place in a program-controlled manner but may also take place by copy machining in the original or also in the enlarged state with the aid of a model pattern.

Reference is made to PCT/CH00/00623 for an automatic machine tool for producing basic frameworks for tooth replacement, in particular for tooth crowns and/or tooth bridges of precise three-dimensional form. The basic frameworks, as these worked ceramic workpieces are called in this document, are produced in a machine tool comprising a machine frame or housing, a workpiece carrier with a rotary shaft, at least one digitalising unit, at least one machining unit with the milling cutters and an electronic computing and control unit for all the drive members. A holding device, not shown in detail, for the blank is formed which is fastened to the rotary shaft of a displacement unit with three axes of translation in the x, y, and z direction. Digitalisation of a preparation model clamped on the same rotary shaft and the machining of the blank are carried out on the same machine tool at different times. Prior to machining, the blank the machining paths for the blank are calculated from the determined and stored digitalisation data and a preselected, material-specific scaling factor.

DE A1 4436231 describes a tablet-like blank for a tooth crown, which is embedded in a ring and held by way of this in a clamping device for machining. The purpose of this device is so that only a very small residual quantity of the very expensive materials used in dental technology occurs when the ceramic workpiece is worked out from the blank, in that the diameter of the blank can be reduced. The blanks of exclusively tablet-like shape can no longer be machined with complete design freedom owing to the ring, so even the minimum material consumption is finally also impaired. This holding device with a ring is also intended for the production of tooth crowns and is not suitable for the production of long tooth bridges.

EP A2 0982009 also describes a holder for a blank for producing a tooth replacement part. The blank does not project beyond the support body in any direction, so the freely accessible surface is small. The holder is to protect the blank, in particular during automatic conveying in magazines and the like, which is obviously to the detriment of processing freedom.

The object of the present invention is to provide a holding device of the type mentioned at the outset which, independently of the geometry, provides adequate protection against any excessive mechanical stresses and deformations even for elongate blanks. As large as possible a proportion of the surface of the blank should also be freely accessible for the material-removing machining and the worked out ceramic workpiece should be held securely.

SUMMARY OF THE INVENTION

With respect to the holding device, the object is achieved according to the invention in that a narrow frame is fastened in an adhesive bond over at least a part of the periphery of the blank which is held without tension in the region of a plane comprising the longitudinal central axis of the blank, the frame only covering a small part of the surface of the blank and in turn being held detachably and secured against slipping in a stable holder with a clamping adapter, and this combination is fastened non-rotatably and secured against slipping in the machine tool. Special and further embodiments of the holding device are the subject of the dependent claims.

A blank which can be machined in a holding device according to the invention may have any desired geometric shape and be present in the green or sintered-on state. Perpendicular to the longitudinal central axis of the blank, it may be round or polygonal in design, in the latter case with two respective parallel side faces, in particular square, rectangular, hexagonal or octagonal. With respect to material, the cylindrical or prismatic blanks consist preferably of at least one metal oxide, in particular Al2O3, TiO2, MgO, Y2O3 and/or zirconium oxide mixed crystal. Reference is also made in this respect to WO99/47065.

According to the invention the porous ceramic blanks are at least partially surrounded by a narrow frame which is in turn held in a stable holder in a machine tool. The narrow frame extends such that the longitudinal central axis of the blank is in the region of the plane of the frame. Quantitatively, the thickness of the frame, measured in the tangential direction of a cylindrical blank, for example, is 1 to 8 mm, preferably 3 to 6 mm. The thickness of the frame is suitably selected such that at most 25%, in particular at most 15%, of the surface of the blank is covered.

With respect to the longitudinal central axis the frame radially has a width easily allowing clamping in the stable holder, in other words preferably in the region of 3 to 10 mm. In most cases the frame is designed to be peripherally continuous and regular. However, it can be much wider on a longitudinal or narrow side of the blank, for example 15 mm. It may then be held exclusively in this region by the holder.

Whether peripherally continuous or only partially formed, the frame is continuously connected to the blank preferably on all the faces facing the blank surface. The bond is provided in such a way that the blank itself does not experience any stresses. The inner faces of the frame form an aperture, which is greater by the adhesive gap than the blank to be inserted. A bonding agent, preferably a two-component adhesive, is inserted into the narrow gap between the frame or the individual parts thereof.

The frame or the individual parts thereof may be roughened on the interior or coated with a bonding agent.

According to a preferred variation, the frame is designed uniformly, i.e. with a constant cross-section along a longitudinal axial peripheral line and designed peripherally complete along this entire periphery. A frame designed in one piece may also be U-shaped, however, with the sides extending substantially over the entire dimension of the blank. According to this variation a longitudinal or narrow side of the blank may be completely free. With respect to machining freedom, this is an advantage. It is disadvantageous that no holding webs can be formed on positions without a frame.

However, it is within the range of the present invention that the frame is composed of individual pieces which are glued to the blank in each case. The individual pieces may rest on one another or be glued on with a small spacing from each other.

However it is designed, the frame suitably consists of a mechanically rigid plastics material or an easily machinable metal, for example aluminium.

Whether the frame can be changed in its dimensions, for example by legs which can be inserted in one another, or the adhesive is applied in recessed grooves of the blank, or other variations are carried out, is left to the judgement of the person skilled in the art and takes place in particular according to economical viewpoints.

The blank with a frame applied suitably by the manufacturer is detachably clamped by a method per se, in a mechanically stable holder having a clamping adapter for a machine tool, in particular a mandrel with rotation-preventing means for insertion or a plate for flanging-on. It is essential here that the frame is clamped in such a way that the blank itself experiences no stresses. In other words the holding forces of the blank frame in the holder are not directed in the direction of the blank surface. This may take place, for example, with a closed or U-shaped clamping frame, or else with two clamping jaws in the case of an appropriate design of the frame.

Clamping the frame in the holder may be facilitated by a special design of the outside of the frame or parts thereof, in that suitable faces for receiving are formed, for example in the form of spheres, pyramids, hemispheres, or also in dovetail or roof form, which are also used to determine the position.

With respect to the method, the object is achieved according to the invention in that a preselected workpiece is continuously exposed from the ceramic blank until only holding webs which can be freely selected according to position and number are formed which end directly on the residual material of the blank in the region of the frame or on the frame.

During machining, the connection between the workpiece and the residual material becomes weaker and weaker until on completion of machining the workpiece is only connected by the holding webs to the residual material or frame. Machining is not limited as in one-sided holding by preselecting the feed direction and/or the machining. The workpiece may be held securely until completion of machining; there is no risk of uncontrolled breaking out of the workpiece.

Because of the small thickness of the frame in relation to the diameter of the blank, the desired maximum free accessibility of the blank surface is ensured. The type of possible blank cross-sections is not restricted; suitable blank cross-sections can be selected. The length of the blank may also be adapted for workpieces with larger clamping lengths, for example multi-membered tooth bridges. The diameter of the blank may also be appropriately adapted to larger and smaller workpieces. Sharply bent large tooth bridges are particularly demanding, in which the holding device according to the invention has already proved itself in tests.

The holding device according to the invention may be used advantageously in particular for producing solid ceramic tooth replacements, in particular tooth crowns or tooth bridges.

The advantages of the invention can be summarised briefly as follows. The peripheral frame only covers the surface of the blank to a small extent, in other words it provides a surface for machining which has maximum free accessibility. The at least partially peripheral frame also offers the possibility of determining holding webs with respect to number and position in the region of the frame. A holding web configuration adapted to the individual workpiece shape, for example tooth shape, is made possible. Thus, the introduction of the machining forces into the holder is optimised. In addition, the stresses resulting from the machining are distributed over the area and not only concentrated on a small part.

BRIEF DESCRIPTION OF THE DRAWINGS

The invention will be described in more detail with the aid of embodiments shown in the drawings, these also being the subject of the dependent claims. The drawings show schematically:

FIG. 13 a lower part of a holder according to FIG. 12,

FIG. 14 a plan view of a blank clamped in a holder,

FIG. 15 a radial section XV—XV according to FIG. 14, and

FIG. 16 a diagrammatic representation of the transmission of the clamping force.

DETAILED DESCRIPTION

Figure 1:
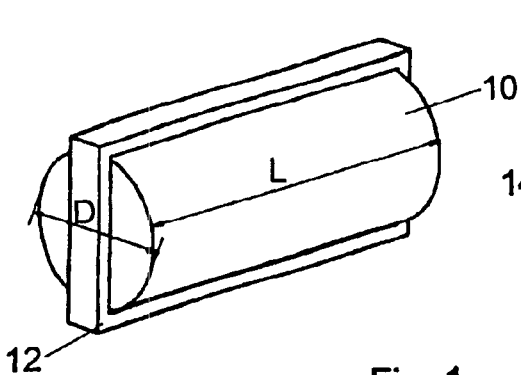
FIG. 1 a ceramic blank with a frame in a perspective view.

FIG. 1 shows a porous ceramic blank 10 of cylindrical shape. In the present case it consists of zirconium oxide, has a diameter D of 25 mm and a length L of 48 mm. In the region of the longitudinal central axis A (FIG. 3) a closed frame 12, which is rectangular in cross-section, and consisting in the present case of rigid plastic material, is glued on. The frame has an external measurement of 56×32×5 mm, the corresponding internal measurements are 48.5×25.5×5 mm. An average adhesive gap 14 (FIG. 4) of 0.25 mm filled with a rapid adhesive 16, for example the two-component adhesive Araldite® from Ciba-Geigy Corporation, results therefrom. With a frame thickness d of 6 mm a degree of covering of the blank surface of 21% is produced, with a thickness d of 3 mm a degree of covering of 10%. With other blank dimensions and shapes the measurements of the frame are correspondingly adapted, the adhesive gap remaining roughly the same, however.

Figure 2:
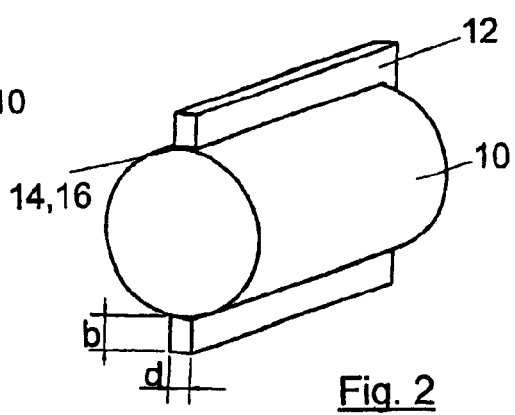
FIG. 2 a variation according to FIG. 1.

A variation according to FIG. 2 differs from FIG. 1 in that the frame 12 with a thickness d and a width b is not closed, but is U-shaped in design. The two sides of the frame are generally roughly flush with the cross-sectionally circular, free end face of the blank 10, but they may be shorter or longer in design.

Figure 3:
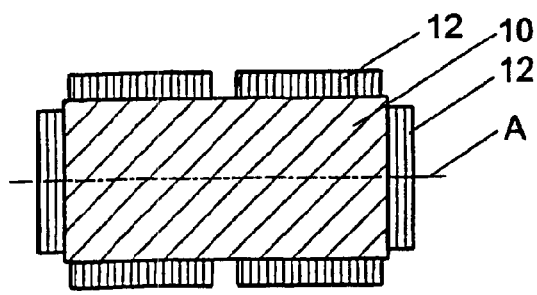
FIG. 3 a further variation in axial section according to FIG. 1.

The variation according to FIG. 3 has a corresponding frame 12 which is, however, glued in pieces to the blank 10.

Figure 4:
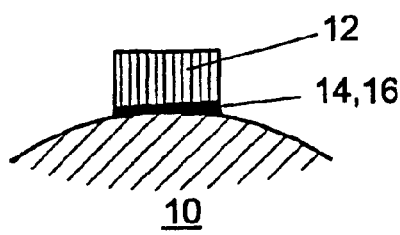
FIG. 4 a detail in the region of the frame, in radial section.

FIG. 4 illustrates the gluing of the frame 12 to the blank 10, the adhesive gap 14 being filled with an adhesive 16.

Figure 5:
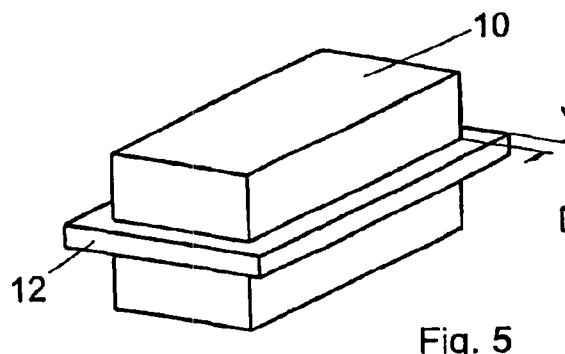
FIG. 5 a right parallelepiped blank in perspective view.

In the embodiment according to FIG. 5, the blank is right parallelepiped in design, the frame 12 is designed to be widened on the rear end face to a width b, so that clamping jaws can engage during holding.

Figure 6:
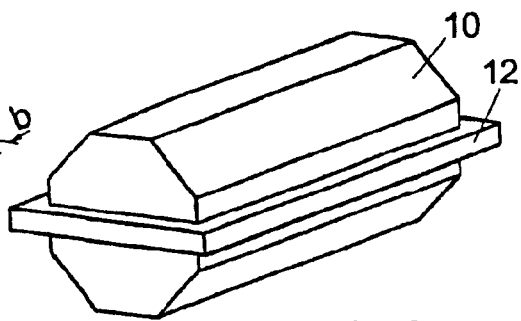
FIG. 6 a variation according to FIG. 5.

A blank 10 according to FIG. 6 is designed octagonally in cross-section, as in FIG. 5 there are in each case two parallel opposing planes to which the peripheral frame 12 is glued.

Figure 7:
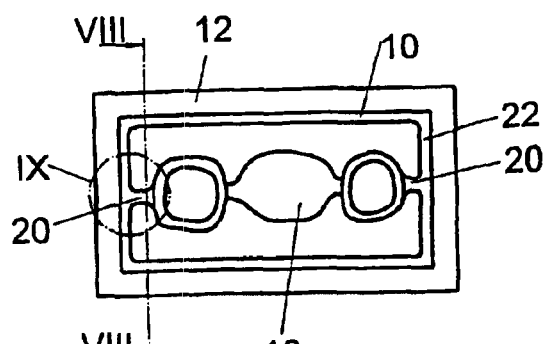
FIG. 7 a plan view of a worked out workpiece.
Figure 8:
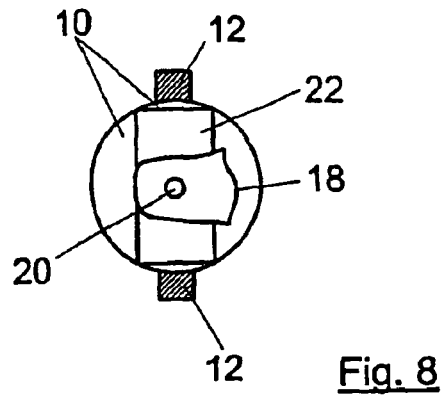
FIG. 8 a lateral view according to FIG. 7.

FIGS. 7 and 8 show a workpiece 18 worked from a blank 10, of which only some remains can be seen, in the present case a three-membered basic framework of a tooth bridge. The workpiece 18 is held by two end-face holding webs 20 and is connected to the remaining residual blank 10, 22 in the region of the frame 12. Two end face residual discs 22 of the blank 10 may remain as residual material, if the blank is not completely machined with respect to its longitudinal axis. Residual material on the frame 12 protects the machining tools from contact with the frame. Additional protection of the machining tool from breakage on contact with the frame occurs if it is made from plastics material and not metal.

Figure 9:
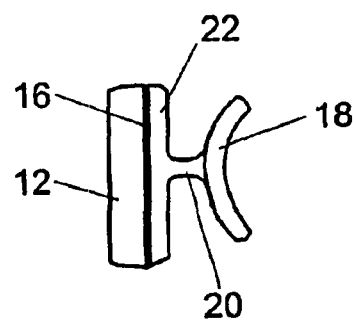
FIG. 9 a detail IX according to FIG. 7.

The region IX according to FIG. 7 is shown enlarged in FIG. 9, an alternative direct connection of the holding web 20 to the frame 12 without a residual disc 22 is shown by a broken line. On completion of machining of the blank, the webs 20 are separated from the workpiece 18 and the point of separation of the workpiece is ground smooth.

Figure 10:
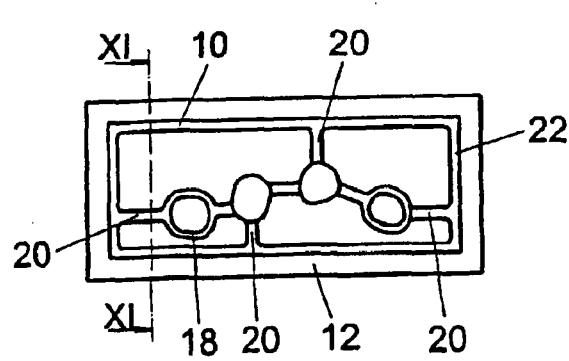
FIG. 10 a variation of a workpiece according to FIG. 7.
Figure 11:
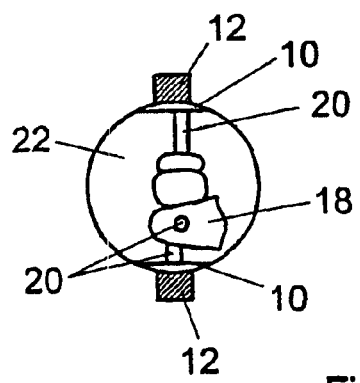
FIG. 11 a lateral view according to FIG. 10.

The workpiece 18, a four-membered tooth bridge in cavital plan view according to FIG. 10 and in sectional view according to FIG. 11 (section XI—XI in FIG. 10) is, however, designed to be substantially more complicated and has four holding webs 20 in total, of which two are connected to the end face 22 and two with surface remains of the blank 10, in each case in the region of the frame 12.

It is of essential significance to the invention that the forces which act on the workpiece 18 are removed by way of the holding webs 20 according to FIGS. 7 to 11 by way of the respective bonding agent 16 into the frame 12. The residual blank or the workpiece 18 is thus held securely inside the frame 12. This may take place by a direct or indirect connection of the holding webs 20 to the frame 12, for example by a residual disc 22. In this respect a closed frame provides the preferred solution with respect to stability and connection possibilities of the holding webs 20.

Figure 12:
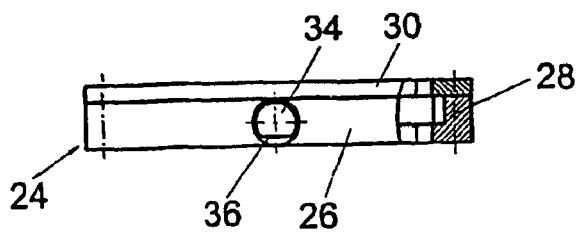
FIG. 12 a partially cut open lateral view of a holder.

A holder 24 which is shown in FIGS. 12 and 13 for the frame 12 of blanks 10 is substantially formed in two parts, FIG. 13 showing the lower holder part 26 having a peripheral shoulder 28. The frame 12 of the blank 10 is inserted into the cup-shaped recess, formed from the peripheral shoulder 28 in the lower holder part 26. The upper part 30 of the holder, a dimensionally identical flat cover, is pressed onto the lower part of the holder 26 when the frame 12 is inserted. In the process, and this is of essential significance, only the frame 12 is clamped by application of a clamping force. No clamping forces are transmitted to the blank 10. Clamping takes place in the present case because of screws provided in the four corners, the corresponding screw holes 32 being drawn in. A clamping adapter 34 is fastened to the lower holder part 26, the adapter 34 being held by way of a mandrel in the chuck of the rotary shaft of a machine tool. A rotation-preventing device 36 is also provided and is designed as a flat surface or a bolt.

A holding device 42 according to FIGS. 14 and 15 consists of the holder 24 consisting of the lower holder part 26, the upper holder part 30, the clamping adapter 34 and screws 32, with the inserted combination of blank 10 and frame 12. The holder 24 is stable and may be manufactured from aluminium, its alloys or otherwise steel. The connection between the holder 24 and frame 12 is detachable, so the frame 12 together with the blank 10 can be simply inserted or else removed again. The holder 24 does not contact the ceramic blank 12 in the process. The frame 12 is inserted into the lower holder part 26 which has a suitable, cup-shaped recess for it. The upper holder part 30 is placed on the lower holder part 26 and fastened thereto, as already shown, with the screws. In the process the frame 12 is clamped between the lower holder part and the upper holder part. The flat surface on the clamping adapter 34 is a rotation prevention device 36. The clamping adapter 34 may be arranged on the longitudinal or narrow side.

FIG. 16 shows the clamping forces F by arrows 38, 40; they act in the tangential direction with respect to the blank. In other words the action direction of the clamping forces F is not directed onto the blank 10. The holder 24 together with the combination of the frame 12 and blank 10 are held in a machining machine by inserting the clamping adapter 34 in the machine side, so the blank can be machined. The predefined position is fixed by a rotation-preventing device 36 (FIGS. 12–14).

According to variations which are not shown, the holder 24 extends only by way of a part of the frame 12, for example in a U-shape. Also, in the case of a frame 12 which is widened on the end face, only two clamping jaws may be formed.

What is claimed is:

1. In combination, a porous ceramic blank having a longitudinal axis A and holding means, said holding means comprises (1) a frame which is adhesively bonded to at least a portion of a surface of the blank wherein the blank is held by the frame without tension in a region of a plane which includes the longitudinal axis A, (2) a holder wherein the frame is detachably secured against slipping in the holder, and (3) clamping adaptor means for securing the holding means in a machine tool for the material-removing machining of the blank.

2. The combination according to claim 1, wherein the blank is perpendicular to the longitudinal axis (A), is round and has two substantially parallel side faces.

3. The combination according to claim 1, wherein the blank comprises a ceramic material selected from the group consisting of Al2O3, TiO2, MgO, Y2O3, zirconium oxide, and mixtures thereof.

4. The combination according to claim 1, wherein the frame covers at most 25% of the surface of the blank and has a thickness (d) between 1 to 8 mm.

5. The combination according to claim 4, wherein the frame has a width (b) of between 3 to 20 mm.

6. The combination according to claim 1, wherein the frame is one of closed and U-shaped in configuration having sides extending over substantially the length of the two substantially parallel side faces of the blank.

7. The combination according to claim 1, wherein the frame comprises a plurality of sections adhered to the surface of the blank, wherein the sections are at a distance from one another.

8. The combination according to claim 1, wherein a narrow gap between the frame and the blank is filled with a bonding agent.

9. The combination according to claim 1, wherein means for receiving the holder are formed on the frame.

10. The combination according to claim 1, including indicia is provided on the frame.

11. The combination according to claim 1, wherein the holder comprises a closed frame having a lower holding part and an upper holding part for receiving the frame.

12. The combination according to claim 11, wherein the lower holding part has a recess for receiving the frame and the upper holding part clamps the frame in the recess by means of fasteners.

13. A method for machining a dental piece from the blank of the combination of claim 1, comprising the steps of machining the blank to form web between the dental piece and a portion of the blank bonded to the frame.

* * * * *